(12) United States Patent
Edgson et al.

(10) Patent No.: US 6,967,002 B1
(45) Date of Patent: Nov. 22, 2005

(54) METHOD AND APPARATUS FOR PRODUCING A STERILE FLUID

(75) Inventors: Raymond Anthony Edgson, Litlington (GB); Michael John Dunkley, Cambridge (GB); Richard J. Hammond, Cambridge (GB); Eric Wilkinson, Cambridgeshire (GB)

(73) Assignee: Gambro Lundia AB (SE)

( * ) Notice: Subject to any disclaimer, the term of this patent is extended or adjusted under 35 U.S.C. 154(b) by 0 days.

(21) Appl. No.: 10/088,310

(22) PCT Filed: Apr. 4, 2000

(86) PCT No.: PCT/SE00/00630

§ 371 (c)(1),
(2), (4) Date: Jul. 18, 2002

(87) PCT Pub. No.: WO01/19413

PCT Pub. Date: Mar. 22, 2001

(30) Foreign Application Priority Data

Sep. 16, 1999 (SE) .............................. 9903331

(51) Int. Cl.$^7$ ............................ A61L 2/00; B01J 19/00; B01D 21/30; B01D 35/18

(52) U.S. Cl. ................. 422/1; 422/3; 422/38; 422/40; 422/255; 422/261; 422/307; 422/308; 210/143; 210/149; 210/175

(58) Field of Search ............ 422/1, 3, 38, 40–41, 422/255–256, 261, 292, 307–306; 210/143, 149, 175

(56) References Cited

U.S. PATENT DOCUMENTS 5,032,265 A 7/1991 Jha et al.
5,603,894 A 2/1997 Aikus et al.
6,309,673 B1 * 10/2001 Duponchelle et al. ...... 424/717
6,579,494 B1 * 6/2003 Chevallet et al. .............. 422/3

FOREIGN PATENT DOCUMENTS

| EP | 0 428 009 B1 | 5/1991 |
|---|---|---|
| GB | 1 450 030 | 9/1976 |
| GB | 1 504 334 | 3/1978 |
| GB | 2 034 584 | 6/1980 |
| WO | WO-93/09820 A1 | 5/1993 |
| WO | WO-96/13279 A1 | 5/1996 |
| WO | WO-97/05852 A1 | 2/1997 |
| WO | WO-98/07328 A2 | 2/1998 |
| WO | WO-99/27885 A1 | 6/1999 |
| WO | WO-00/24433 A1 | 5/2000 |

* cited by examiner

Primary Examiner—Robert J. Warden, Sr.
Assistant Examiner—Monzer R. Chorbaji
(74) Attorney, Agent, or Firm—Lerner, David, Littenberg, Krumholz & Mentlik, LLP

(57) ABSTRACT

A method and apparatus for producing a sterile medical solution is disclosed. The method includes providing at least two components, a first component including bicarbonate ions and a second component including glucose or calcium ions, preheating the first component to a first temperature and the second component to a second temperature, heat sterilizing the first and second components separately to a third and fourth temperatures respectively, the third and fourth temperatures being sterilizing temperatures for the first and second components, maintaining the first and second components approximately at their respective third and fourth temperatures, so as to sterilize the first and second components, cooling the first and second components and delivering the first and second components to a mixing device.

17 Claims, 2 Drawing Sheets

METHOD AND APPARATUS FOR PRODUCING A STERILE FLUID

FIELD OF INVENTION

The present invention relates to a method and an apparatus for producing a sterile fluid as a medical solution. More specifically, the invention relates to a method and apparatus for producing a sterile medical solution comprising components, which cannot be sterilized together.

PRIOR ART

Medical solutions intended for mammals, specifically for use in humans, are required to be sterile before being infused into or applied to the mammal.

One available method for sterilizing a solution is to pass the solution through a sterilizing filter, such as an ultrafilter.

Another available method for sterilizing a solution is to heat the solution to a sterilizing temperature and to hold the solution at the sterilizing temperature during a sterilizing time. To obtain a sterile medical solution intended for infusion, the solution is normally heated in an autoclave to 121° C. for 20 minutes to thereby produce said sterile medical solution. After the sterilizing time has elapsed, the solution should be cooled to a physiologically acceptable temperature before infusion.

Known methods and apparatus for heat sterilizing a solution are disclosed in for example GB 1450030, GB 1504334, GB 2034584 and U.S. Pat. No. 5,603,894. These prior art publications describe the preparation of a medical solution starting from tap water by producing pure water via a reverse osmosis device, mixing a concentrate with the pure water to produce a non-sterile medical solution, passing the non-sterile medical solution through an on-line autoclave and delivering the sterile medical solution to a recipient, such as a storage bag or a patient.

In the prior art, the complete medical solution is first prepared in a non-sterile condition and then passes through an autoclave. If the medical solution comprises heat sensitive components, these must not be exposed to too high a temperature. Normally, the temperature is increased up to the sterilizing temperature and the medical solution is maintained at the sterilizing temperature for a sterilizing time. If the temperature is 121° C., which is normal in an autoclave, the sterilizing time is 20 minutes to obtain a sterilizing dose $F_0$ of 20 minutes, see below for further details. Since the sterilizing effect is approximately exponential, an increase of the temperature by 10° C. means a lowering of the sterilizing time by ten times. If a sterilizing temperature of 131° C. is used, the sterilizing time should be 2 minutes, and if a sterilizing temperature of 141° C. is used, the sterilizing time should be 12 seconds, in order to obtain a sterilizing effect $F_0$ of 20 minutes.

If the medical solution comprises a heat sensitive component, like glucose, that component will deteriorate during the heat treatment. An example of a medical solution containing a heat sensitive component is dialysis fluid for peritoneal dialysis (PD). The decomposition or heat deterioration starts 25 at a much lower temperature than the sterilizing temperature and is present also at room temperature. In order to safeguard the heat sensitive material, very short heating and cooling periods are desired so that the time/temperature profile becomes more or less rectangular. This is of greater importance if high sterilizing temperatures and short sterilization times are used.

If the solution comprises components which may not be sterilized together, these previous methods cannot be used. Such components is for example glucose and bicarbonate, since a solution comprising these two components forms glucose degradation products which may be toxic.

It is known to produce sterile medical solutions by including the medical solution in a bag and placing the bag inclusive of the medical solution in an autoclave for heating and sterilization.

A variant of this method is described in WO 93/09820, in which the medical solution is divided in two portions, one comprising glucose at high concentration and the other comprising the rest of the solution, including a buffer. The double bag is heat sterilized in an autoclave. Shortly before use, the contents of the two chambers are mixed to produce the sterile medical solution. In this way, the heat sensitive component, glucose, can be autoclaved under more appropriate conditions such as at a low pH of approximately pH=3.2 and at a high concentration of approximately 50%, i.e. 500 g glucose per liter glucose solution.

A variant of the same methods is described in WO 97/05852 disclosing a three-chamber-bag, in which two of the chambers comprise glucose solution and the third chamber comprise the rest of the solution. The glucose chambers may also include ionic components like calcium, magnesium and sodium.

A further variant is described in WO 99/27885.

In the afore mentioned concepts, the glucose portion is sterilized separately from the remaining portion of the solution. However, in order to fully sterilize the large compartment, the small glucose compartment may be over sterilized resulting in deterioration of the heat sensitive component. A remedy for that problem is described in Swedish patent application SE 9803627-0, filed at the Swedish Patent Office Oct. 23, 1998. In these methods, the glucose component is sterilized separately from the buffer component, which may be sodium lactate and/or sodium bicarbonate.

The problem of deterioration of a substance during autoclaving is also recognized in other fields of use, such as the production of sterile milk products. In order to obtain a fast heating and cooling of the product, it is not sufficient to use heat transfer via a heat transferring surface, like a heat exchanger. Instead, the product is mixed with steam at a predetermined temperature and pressure to condense the steam in the milk product. The milk product is sterilized by retention in a holding zone for a certain time period and at a temperature of 120–150° C., and is then transferred to a flash cooling step, in which water is evaporated in an evaporation chamber to rapidly cool the product. Such a process is described in, for example, WO 98/07328.

Sterilization by filtration is disclosed in e.g. U.S. Pat. No. 5,032,265, which discloses preparation of RO water from potable water, mixing the RO water with a concentrate, and passing the diluted concentrate through a microfilter to produce a sterile medical solution such as a PD solution.

DISCLOSURE OF INVENTION

A first object of the present invention is to provide a method and device for producing a sterile fluid, which is composed of components which normally cannot be sterilized together.

Another object of the invention is to provide a method and device for producing a sterile medical solution having a gentle treatment of the heat sensitive component.

A third object of the present invention is to provide a method and device for heat sterilizing a medical solution in which the time/temperature profile for heating the heat sensitive component is essentially rectangular.

Thus, there is provided, according to the invention, a method of producing a sterile medical solution, characterized by providing ingredients for said solution as at least two components and passing each component separately through a sterilizing device for sterilizing said component and delivery to a mixing device. In this way, components that cannot be sterilized together may be included sequentially in the final medical solution.

Preferably, the sterilizing step is a heat sterilizing step, comprising heating said component in a first preheating step to a first temperature, heating said component to a second sterilizing temperature, maintaining said component approximately at said second sterilizing temperature for a sterilization time, cooling said component, and delivery of said component to a mixing device.

The first component may comprise bicabonate ions and the second component may comprises glucose.

Alternatively, the first component may comprise bicabonate ions and the second component may comprise calcium ions.

Each component may be provided as a concentrate to be mixed with substantially water before or after the sterilization step.

One of the components may comprise glucose at a low pH of below about 5, or has preferably a pH of about 3.

The invention also relates to a method comprising providing said components as at least three components in concentrated form;
providing a flow of water;
introducing one of said concentrated components into said flow of water for dilution thereof;
heat sterilization of the diluted component by passing said diluted flow of the component through an on-line heat steriliser; and
mixing the sterilized diluted component in a mixing device.

A second concentrated component may be provided to said flow of water before the on-line heat sterlizer.

More specifically the components may include electrolytes, selected from the group of substances comprising: sodium chloride, calcium chloride, magnesium chloride, potassium chloride, sodium bicarbonate, sodium lactate and glucose (or dextrose).

Normally, the temperature is above the boiling temperature at normal atmospheric pressure and, thus, the first and second components are maintained at a high pressure sufficient to prevent boiling.

In an embodiment, the first and second components are provided as flows of fluid.

According to the invention, the complex fluid is divided in several fluid components, which are sterilized separately and sequentially and then mixed to the complex fluid.

BRIEF DESCRIPTION OF THE DRAWINGS

Further objects, advantages and features of the invention will appear from the following detailed description of several embodiments shown on the drawings.

DETAILED DESCRIPTION OF EMBODIMENTS OF THE INVENTION

Figure 1:
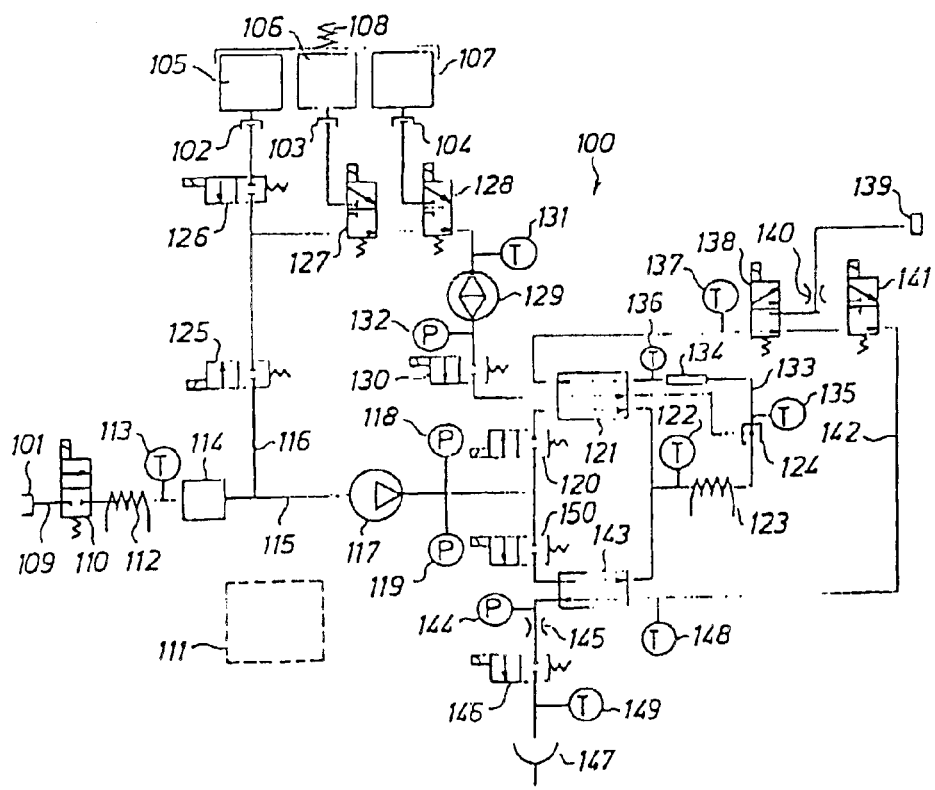
FIG. 1 is a schematic view of a first embodiment of a device for sterilizing a complex fluid according to the invention.

The fluid to be sterilized comprises at least two components or portions. According to the invention, the two components are delivered separately and sequentially to a heat sterilizing device.

The sterilizing dose is a function of temperature and time and is defined according to the formula:

$$F_0 = \int_0^t 10^{(T-121)/10} dt$$

in which
$F_0$=the sterilization dose in minutes
T=temperature
t=time

If the sterilizing temperature is 121° C. and the time is 20 minutes, a sterilization dose of 20 minutes is obtained. If the sterilizing temperature is 141° C. and the time is 12 seconds, a sterilization dose $F_0$ of 20 minutes is also obtained. A sterilizing dose $F_0$ of 20 minutes is considered sufficient, however, in certain applications, a sterilizing dose $F_0$ of 10 minutes or even lower may be sufficient.

The sterile fluid may be used as a peritoneal dialysis fluid to be delivered to the peritoneal cavity of a patient. Other medical fluids may be produced by the apparatus according to the invention, such as hemodialysis solutions, infusion solutions used in hemodiafiltration or hemofiltration, replacement fluids for infusion in the blood, wound irrigation solutions, rinsing solutions etc. Moreover, nutrition solutions often comprises amino acids, which are heat sensitive, and glucose, which is heat sensitive, and cannot be sterilized together with amino acids. Certain drugs, such as insulin, may be produced or included in a fluid administered to a patient, and the drug component may be heat sensitive. Certain medical fluids comprise peptides, proteins or fragments thereof, which normally are heat sensitive. Preservation fluids for blood component handling may also comprise heat sensitive components, at least glucose. In certain cases, glucose is replaced with or complemented with glucose polymers, di-sacharides, tri-sacharides etc. Certain carboxylic acids are heat sensitive and may be included in such fluids. Solutions comprising calcium or magnesium ions and carbonate or bicarbonate ions may precipitate at exposure to a sterilizing temperature, and need to be sterilized with the carbonate or bicarbonate ions separate from the calcium or magnesium containing solution. Furthermore, glucose and carbohydrates may not be heat sterilized together with bicarbonate, without formation of degradation products.

It is known that glucose decomposes when exposed to heat, and is thus a heat sensitive component of the fluid. Glucose also decomposes during storage. It is known that several factors influence the decomposition of glucose, among which are pH, temperature, time, glucose concentration and mixing with certain ionic components, such as bicarbonate. Glucose decomposes into components, some of which may be more or less toxic or are able to induce toxic reactions by including precursors for such reactions. If the resulting fluid is to be used as a medical fluid for infusion into a human being or other mammal, the toxic components or precursors should be minimised.

In order to sterilise the fluid it is necessary to expose the fluid to sterilizing conditions. There are several methods available, such as heat sterilization (autoclaving), filter sterilization and other methods.

During heat sterilization, it is known that decomposition of glucose can be minimized if glucose is sterilized during a short time at a high temperature. The rationale is that the decomposition reaction is less sensitive to high temperature than the sterilizing reaction.

In order to minimize the decomposition before sterilization, it is advantageous to store the glucose containing fluid at a low pH and at a high concentration, which is suggested according to the invention. The pH may be from 2,6–5,0 and preferably pH=3,2. The concentration may be above 10%, 15% or 20% while 40%–50% being preferred, calculated as weight of glucose per liter solution. Furthermore, the glucose containing portion should not comprise bicarbonate ions. However, calcium ions may be included in the glucose portion as well.

The sterilization of the glucose component may take place during a short time and at a pH of below about 5,5 and at a final dilution concentration. It is believed that the short time is of greater importance than the other factors for avoiding decomposition into toxic components of glucose during the sterilization process. However, it is preferred to maintain the pH below 4 or preferably at 3,2 during the sterilization.

It is also recognized that glucose may decompose into precursors for AGE, advanced glucosylation end products. When a glucose solution comprising precursors for AGE contacts proteins in the body, a non-enzymatic reaction takes place resulting in AGE formation. The long term effect of AGE is still not well known. Gentle sterilization of glucose as suggested in the present invention is expected to reduce the level of glucose degradation products of the type of AGE precursors.

A first embodiment of the invention is shown in FIG. 1. From the left, the device 100 comprises a connector 101 for connection to a source of pure water, such as an RO-unit (not shown). The device further comprises three concentrate connectors 102, 103 and 104, which may be integrated into a single connector device. Each of connectors 102, 103 and 104 connects to a vessel or bag comprising a concentrate, such as a first bag 105 comprising a concentrated bicarbonate solution, a second bag 106 comprising electrolytes, such as sodium chloride, magnesium chloride, calcium chloride, and sodium lactate, at a predetermined pH, and a third bag 107 comprising glucose at a concentration of 50%. Of course, the bags include the components necessary for the final solution as discussed in more detail below. The components are divided into separate bags because they cannot be stored together or they cannot be sterilized together, or for other reasons.

Alternatively, one or more of the vessels or bags 105, 106, 107 may comprise a powder instead of a solution in which case appropriate dissolution means may be provided. Of course, four or more bags may be included. In some occasions, only two bags are required.

Conveniently, the bags 105, 106 and 107 are combined into single assembly. The combined assembly of bags is attached to a weighing device 108, so that the weight of the assembly is monitored. The connectors 102, 103 and 104 are attached to the ends of flexible tubes of PVC or other suitable pliable material, so that the connectors and tubes do not significantly influence the weight of the assembly.

The RO inlet connector 101 is connected to a line system including a first inlet line 109. Inlet line 109 is provided with a inlet valve 110, to isolate the device 100 if required. Inlet valve 110 is normally closed, but is opened upon activation by a control device 111 shown by broken lines. The control device may be a computer or microprocessor or any other control device. Normally, it is the control computer of the complete device.

Inlet line 109 further comprises a heater 112 and a temperature sensor 113, which operate together to adjust the temperature of incoming pure water to a predetermined temperature of e.g. 25° C., in order to make the device independent of incoming water temperature, which may vary between 4–25° C.

Inlet line 109 further comprises a flow meter 114 for measuring the complete inlet flow through inlet connector 101, for a purpose to be described later.

Downstream of flow meter 114, inlet line 109 is divided into water line 115 and concentrate line 116. Water line 115 comprises a first pump 117 for increasing the pressure of the water in water line 115 downstream of the pump to a pressure of 2–6 Bar absolute pressure. The pressure is measured by a first pressure sensor 118 and monitored by a second pressure sensor 119. The first pressure sensor 118 is connected to the control system of computer 111, while the second pressure sensor 119 is connected to a parallel supervising system for ensuring the safety of the system. Several of the sensors are duplicated in this manner to provide independent data to the supervisory system or processor, even if not explicitly indicated in the drawings.

Water line 115 further comprises a valve 120 and a primary circuit of a heat exchanger 121. The water in water line 115 is heated from about 25° C. to about 131° C. in heat exchanger 121, at a flow of about 120 ml/min. The temperature of the heated water is monitored by temperature sensor 122. Finally, water line 115 comprises a second heater 123, for heating the water to a still higher temperature, such as about 145° C. The hot water is delivered to a mixing point 124.

In concentrate line 116, there is a valve 125 for connecting the normally closed concentrate line 116 to water line 115. Further downstream, concentrate line 116 comprises three concentrate valves 126, 127 and 128 and a reversible second pump 129. The second pump 129 is arranged to withdraw concentrate solutions or fluids from any one of concentrate bags 105, 106 or 107 depending on the positions of valves 126, 127 and 128. The second pump 129 further increases the pressure of the fluid in concentrate line 116 to a pressure of 2–6 Bar absolute pressure.

Downstream of second pump 129 is arranged a valve 130, and therefrom, the concentrate fluid is delivered to a second primary circuit of heat exchanger 121 in order to preheat the concentrate solution from e.g. room temperature to about 131° C. From heat exchanger 121, the concentrate solution is delivered to mixing point 124.

Upstream of the second pump 129 is arranged a temperature sensor 131 for measuring the temperature of the incoming concentrate fluid, and downstream of the second pump is arranged a pressure sensor 132 for measuring that sufficient pressure has been obtained. As indicated before, these sensors may be duplicated for supervisory purposes.

In mixing point 124, the two fluid lines 115 and 116 are joined so that the heated water in line 115 is mixed with preheated concentrate in line 116, and the mixture is transported in mixed fluid line 133. Mixed fluid line 133 comprises a residence device 134, normally being a length of tube of a length to produce a predetermined residence time at a predetermined rate of flow to effect sterilization of the fluid in the residence device 134. The residence device 134 is preceded by a temperature sensor 135 and followed by a temperature sensor 136. These temperature sensors control the heater 123 to ensure that sterilizing conditions are obtained in the residence device 134, such as a minimum temperature of 141° C. for 12 seconds.

From the residence device 134, the sterilized and mixed fluid is passed to the secondary circuit of heat exchanger 121, at a temperature of approximately 141° C. The sterilized fluid is rapidly cooled to about 37° C.

Downstream of the heat exchanger, mixed fluid line 133 comprises sterilized fluid at a temperature suitable to be delivered to a patient or a storage bag. The temperature is monitored by a temperature sensor 137. Finally, a valve 138 directs, when activated, the fluid to an outlet connector 139, via a restrictor device 140, for lowering the pressure to atmospheric pressure.

The restrictor device may be a small hole in a piece of metal, the hole being dimensioned to reduce the pressure from 6 Bar to 1 Bar at the desired flow rate of, for example, 140 ml/min. An alternative design would be to use a controllable throttle valve, which is controlled by the processor in dependence of pressure sensor readings. A third alternative would be to use a throttle device of the pressure relief type, which adjust the differential pressure over the throttle device to a predetermined pressure drop of, for example, 5 Bar. A fourth alternative would be to use a throttle device controlled to deliver fluid at an output pressure of no more than a predetermined safe pressure of, for example, 1.25 Bar, in which case the pumps are operated to ensure that the pressure before the throttle device is sufficiently high, for example 6 Bar.

It is noted that the on-line autoclave as described is always operated at a predetermined minimal flow rate of not less than a predetermined flow rate, for example 140 ml/min, in order to ensure that the autoclave is maintained sterile. As soon as the flow rate drops below said predetermined minimum flow rate, the sterility conditions may be hampered or the autoclave may not be controlled to operate at proper temperatures. The autoclave may be designed to operate at different flow rates above said minimum flow rate. In order to always maintain a minimal flow rate, any excess fluid produced is sacrificed to the waste.

If the mixed and sterilized fluid cannot be delivered out via the output connector 139, a valve 141 is activated to deliver the fluid to a sump or waste receiver 147 via a waste line 142. Waste line 142 further comprises a primary circuit of a second heat exchanger 143, a pressure sensor 144, a restrictor device 145 and a valve 146 until the fluid is delivered to the waste receiver 147. A temperature sensor 148 arranged upstream of heat exchanger 143 and another temperature sensor 149 arranged downstream of valve 146 are used to measure the temperatures of the waste fluid.

In the sequential operation mode, water is first delivered in inlet line 109 at a constant rate of 120 ml/min from inlet connector 101, via flow meter 114, in which the flow rate is monitored, and via water line 115 and via first pump 117 to raise the pressure so that the boiling temperature of the fluid is above the temperature anywhere in the circuit. If the maximum temperature is about 150° C., the pressure should be above 4.8 Bar or preferably about 6 Bar absolute pressure. The exact pressure is dependent on the adjustment and operation of restriction device 140. The water further passes the mixing point 124 and enters the mixed fluid line 133 and reaches valve 138, which directs the flow to waste line 142, via valve 141 and further to the waste receiver 147. The outlet connector 139 is connected to a recipient, normally a bag.

When all conditions are checked and the device delivers sterilized water, valve 138 is switched to direct the sterilized water to the outlet connector 139 via restrictor 140.

Substantially at the same time, or shortly thereafter, valve 127 in concentrate line 116 is opened and concentrate pump 129 is activated, with valve 130 in an open condition, to pump concentrate fluid from electrolyte bag 106, via heat exchanger 121 to mixing point 124. The concentrate pump 130 is operated to provide a flow rate of approximately 20 ml/min. At the same time, the weight of the concentrate assembly is monitored by weighing device 108. If the intention is to provide 1 liter of final solution and the concentrate fluid in bag 106 has a concentration of 1:40, the flow is continued for about 1 minute and 15 seconds, until the weighing device indicate that 30 a volume of 25 ml has left the bag 106, whereby 25 ml is the amount required from concentrate bag in 1 liter of final fluid (1:40).

Then, valve 127 is switched off and valve 125 is opened for a short time, such as 15 seconds, to rinse the concentrate line 116.

For including the second concentrate, which may be glucose, bag 107 is connected to the concentrate pump by closing valve 125 and opening valve 128. If the glucose concentrate fluid has a concentration of 50%, the concentrate pump is driven 1 minute per percent concentration to be required in the final fluid at 20 ml/min. If 4% is required, which is the maximum contemplated for a PD fluid, the glucose concentrate is dosed during 4 minutes.

After this step, the concentrate line 116 is again rinsed with water, for example for 15 seconds.

Thereafter, the bicarbonate bag 105 is connected. The bicarbonate is normally stored at a concentration of about 1000 10 mmol/l. First, valve 125 is closed and valve 126 is opened so that concentrate pump 130 pumps bicarbonate fluid out of bag 105. The flow rate may be the same, 20 ml/min, and the mixing and sterilization of bicarbonate fluid is discontinued when the weighing device determines that the required quantity has been removed from bag 105. If the final solution should contain 15 mmol/l, the concentrate pump is operated for 45 seconds to take 15 ml of concentrated bicarbonate solution out of bag 105.

Finally, the concentrate line is rinsed once again and water is delivered to the outlet connector, until the final volume of fluid has been delivered to the bag connected at the outlet connector, which is determined by flow meter 114 in combination with the weight losses measured by weighing device 108 and calculated into volumes by computer 111, taking into account the different densities of the concentrate fluids.

This final filling of water also means that the mix of fluid in the bag connected to the outlet connector is agitated and mixed thoroughly.

During the complete sterilization process described above, valves 138 and 141 are maintained in the same position directing all fluid to the outlet connector 139. Thus, all fluid produced is delivered to the receiver, thereby minimising the time required for the preparation of the complete fluid.

In the example above, 1 liter of final solution has been prepared, but in PD it is more normal that 2 liters are generated each time, or any other volume as required by the user.

It is contemplated that the concentrate fluid bags may include concentrate fluid required for a final fluid volume of 12–25 liters or more if required. Then, the above sequence is repeated for each batch of 2 liters to prepare.

In certain applications for PD, bicarbonate is not used, but lactate is used as the sole buffer. In that case, the third bag in the concentrate assembly is unnecessary, and only two bags may be used. In that case, valve 126 is always closed.

To prepare one batch of 1 liter (1,5% glucose concentration), takes about 7 minutes and 45 seconds, supposing that the RO unit delivers pure water at 120 ml/min and 25 ml electrolytes, 15 ml bicarbonate and 30 ml glucose are used.

In the above example indicated in connection with FIG. 1, the bicarbonate concentrate was sterilized at a concentration of about 140 mmol/litre(1000×20/140). However, there is a risk that carbon dioxide is formed during heat sterilization at such a concentration, and thus, the concentrate pump may be operated at a lower speed during sterilization of bicarbonate fluid.

In FIG. 1, the concentrate fluid is preheated to quite a high temperature. This is performed in an efficient heat exchanger 121 in which the heating fluid is the final sterilized fluid in the secondary circuit of the heat exchanger. Thus, the heat exchanger cannot have any point with higher temperature than the sterilizing temperature, and decomposition of the heat sensitive component is minimised. The further heating to the final sterilization temperature, i.e. from about 131° C. to about 141° C. takes place by the method of mixing with a fluid having a slightly higher temperature. Thus, the heat sensitive fluid component is never exposed to harsh conditions, such as hot points having excessive high temperatures, as may appear in an electric heater. Thus, favourable conditions for less formation of degradation products are obtained. The temperature difference between the primary and secondary circuits of the heat exchanger is about 10° C., which is possible to obtain without excessive long residence times in the heat exchanger.

In FIG. 1, there is a circuit for sterilizing the equipment before use. In water line 115, a parallel circuit to valve 120 and heat exchanger 121 is arranged comprising valve 150 and the primary circuit of heat exchanger 143. When heat disinfection of the complete steriliser 100 is to be performed before a treatment, valve 120 is closed, valve 150 is opened and heater 123 is operated. The water passes from pump 117 via valve 150 to heat exchanger 143 and further to heater 123 to be heated to a temperature of, for example, 141° C. The hot water passes heat exchanger 121 but is not cooled appreciably since the primary circuit of exchanger 121 is disconnected and has no flow. The hot water after heat exchanger 121 passes through line 133 and via valves 138 and 141 to heat exchanger 143 to give off its heat to the water passing at the primary side thereof. Finally, the water is discharged to the waste via restrictor device 145, which lowers the pressure from about 2–6 Bar to atmospheric pressure.

Thus, the on-line autoclave is self-sterilized and is ready for producing PD fluids. The self-sterilizing step may be performed in about 30 minutes and is initiated under program control to happen shortly before the start of a PD treatment, which is scheduled in advance by a patient. When the self-sterilization process is ready, the machine awaits the arrival of the patient, which connects a disposable set to the outlet connector 139.

Figure 2:
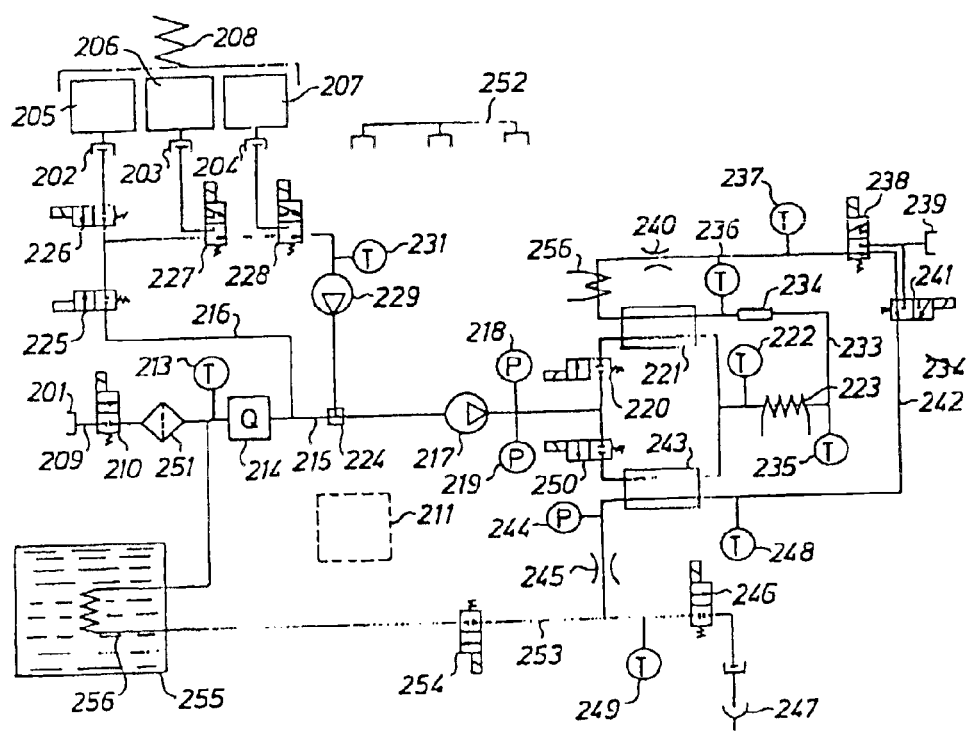
FIG. 2 is a schematic view similar to FIG. 1 of a second embodiment of a device according to the invention.

Another embodiment of the invention is disclosed in FIG. 2. This second embodiment 200 has substantially the same components and the components which are equal or similar to the embodiment 100 of FIG. 1 are given the same reference numeral but the first digit being 2.

Thus, the mixing and sterilizing apparatus of FIG. 2 comprises a connector 201 for connection to a source of pure water, such as an RO-unit and comprises three concentrate connectors 202, 203 and 204, which may be integrated into a single connector device. Each of connectors connects to a vessel or bag comprising a concentrate, namely a first bag 205 comprising an electrolyte solution, such as sodium chloride, magnesium chloride, calcium chloride, and sodium lactate, at a predetermined pH, a second bag 206 comprising glucose, at a concentration of 50% and a pH of above 2,6, preferably about 3,0, and a third bag 207 comprising a buffer, such as sodium bicarbonate and/or sodium lactate. Of course, the bags include the components necessary for the final solution as discussed in more detail below. The components are divided into separate bags because they cannot be stored together or they cannot be sterilized together, or for other reasons.

Conveniently, the bags 205, 206 and 207 are combined into a single assembly. The combined assembly of bags is attached to a weighing device 208, so that the weight of the assembly is monitored.

The RO inlet connector 201 is connected to a line system including a first inlet line 209. Inlet line 209 is provided with a inlet valve 210, to isolate the device 200 if required. Inlet valve 210 is normally closed, but is opened upon activation by a control device 211 shown by broken lines. The control device may be a computer or microprocessor or any other control device. Normally, it is the control computer of the complete device.

Inlet line 209 further comprises a particle filter 251, a temperature sensor 213 and a flow meter 214 for measuring the complete inlet flow through inlet connector 201.

Downstream of flow meter 214, inlet line 209 is divided into water line 215 and concentrate line 216. Concentrate line 216 comprises a valve 225 for connecting the normally closed concentrate line 216 to water inlet line 209. Further downstream, concentrate line 216 comprises three concentrate valves 226, 227 and 228 and a second pump 229. The second pump 229 is arranged to withdraw concentrate solutions or fluids from any one of concentrate bags 205, 206 or 207 depending on the positions of valves 226, 227 and 228. The second pump 229 is a metering pump, which is able to deliver exactly metered quantities or volumes of concentrate fluid. Thus, the second metering pump 229 is a pump of the type constant displacement, such as a ceramic piston pump. The temperature of the concentrate before pump 229 is measured by a temperature sensor 231.

The second pump 129 delivers the concentrate fluid to a mixing point 224 arranged in water line 215. Water line 215 further comprises a first pump 217 for increasing the pressure of the now diluted concentrate in water line 215 downstream of the pump to a pressure of 2–6 Bar absolute pressure. The pressure is measured by a first pressure sensor 218 and monitored by a second pressure sensor 219. Thus, the concentrate metered by the second pump into the water flow in water line 215 is diluted by a factor dependent on the flow rate of the first pump 217 and the second pump 229. The first pump 217 is driven at a constant flow rate of about 120 ml/min and the second pump 229 is normally driven at a constant flow rate of about 15 ml/min.

Water line 215 further comprises a valve 220 and a primary circuit of a heat exchanger 221. The diluted concentrate in line 215 is heated to about 131° C. in heat exchanger 121, at a flow rate of about 120 ml/min. The temperature of the heated diluted concentrate is monitored by temperature sensor 222. Finally, water line 215 comprises a second heater 223, for heating the diluted concentrate to a still higher temperature, such as about 141° C., as measured by a temperature sensor 235. After the second heater 223, the diluted concentrate reaches a residence device 234, in which the diluted concentrate is maintained for a time period sufficient to cause sterilization thereof. From there, the diluted concentrate is passed to the secondary circuit of heat exchanger 221, at a temperature of approximately 141° C. The sterilized fluid is rapidly cooled to about 37° C. If required, there may be included a further cooler 256.

Downstream of the heat exchanger, line 233 comprises sterilized fluid at a temperature suitable to be delivered to a patient or a storage bag. A restrictor device 240 lowers the pressure to atmospheric pressure. The temperature is monitored by a temperature sensor 237. Finally, a valve 238 directs, when activated, the fluid to an outlet connector 239.

It is noted that the on-line autoclave as described is always operated at a predetermined minimal flow rate of not less than a predetermined flow rate, for example 120 ml/min, in order to ensure that the fluid is maintained sterile.

If the sterilized fluid cannot be delivered out via the output connector 239, a valve 241 is activated to deliver the fluid to a waste receiver 247 via a waste line 242. Waste line 242 further comprises a primary circuit of a second heat exchanger 243, a pressure sensor 244, a restrictor device 245 and a valve 246 until the fluid is delivered to the waste receiver 247. A temperature sensor 248 arranged upstream of heat exchanger 243 and another temperature sensor 249 arranged downstream of valve 246 are used to measure the temperatures of the waste fluid.

So far the apparatus 200 is similar to the apparatus 100 of FIG. 1 except for the mixing point 224, which is in the low pressure area before the first pump, in the apparatus 200 of FIG. 2. Because of this early mixing of the concentrate with the RO water, the following heating in heat exchanger 221 and heater 223 must be as quick as possible, and still be gentle. However, a heat exchanger comprising two coils arranged close to each other, forms an efficient heat transferring unit.

The apparatus 200 is sterilized before use as described above for apparatus 100.

However, apparatus 200 further comprises a lid 252, intended to cover the connectors 202, 203 and 204 when the concentrate bags are un-connected. Before use, the fluid preparation portion of the apparatus may be rinsed and disinfected by circulating fluid from the waste line 242 via a recirculation line 253, controlled by a valve 254. Such fluid is circulated to a heating vessel 255 comprising an electric heater 256 to heat the fluid in the vessel 255 to approximately 85–95° C. The heated fluid is circulated from the vessel 255 to the inlet 25 line 209 in a position downstream of filter 251. From there, the heated fluid is circulated through the flow meter 214, into line 216 to reach valves 226, 227 and 228. These valves are switched to different positions to pass the fluid to the lid 252 and through the lines to disinfect them. Then, the heated fluid is passed through pump 229 and into line 215 to pump 217 and further through the on-line sterilizing device as described in connection with FIG. 1. In this manner, all fluid lines and all parts being in contact with the medical fluid to be prepared are rinsed and heat disinfected, which reduces the risk that bacteria and endotoxins will contaminate the medical fluid.

In order to prepare a PD fluid comprising glucose, a buffer and electrolytes, the bags 205, 206 and 207 may comprise the following ingredients:

bag 205: magnesium chloride, calcium chloride, sodium chloride 5 bag 206: glucose bag 207: sodium lactate and sodium hydroxide, or sodium lactate and sodium bicarbonate.

Furthermore, each bag comprises water so that the substances are in fluid form. The pH in bag 206 comprising glucose is adjusted to above 2,6 and preferably about 3,2. When the glucose is diluted by about 1:7 (15 ml/min concentrate and 105 15 ml/min of RO water), the pH will rise with about 0,8 units to a pH=4,0 if the initial pH was 3,2. The diluted glucose solution is then sterilized at this pH, during a short time period of about 12 seconds.

It is preferred to use a buffer comprising a mixture of lactate and bicarbonate. If only lactate is used, sodium hydroxide is added in order to increase the pH of the final solution to about physiological pH, such as 7,0–7,4.

The apparatus 200 is operated so that each component is sterilized separately and in sequence. In order to enable the production of the medical fluid by sequential sterilization of the components, a mixing bag 257 is added to the outlet 239 as shown in FIG. 2.

If the apparatus is intended to produce 2 liters of PD fluid, comprising 20 mM bicarbonate, 20 mM lactate, 1,23 mM calcium, 0,5 mM magnesium, 140 mM sodium, and 1,5% glucose, at a pH of 7,0–7,4, these parameters are entered in the control device 211. The control device operates the valves and pumps to produce the right amount of concentrate from the first bag 205, the electrolytes, to be passed to the mixing bag through the sterilizing device. Then, concentrate from the second bag 206, glucose solution, is passed to the mixing bag in the right amount. Then, concentrate from the third bag 207 is passed to the mixing bag in the right amount. Finally, the mixing bag is filled with water to obtain the final mixture. This sequential sterilization means that the sterile fluid may comprise glucose, bicarbonate and calcium, which cannot be sterilized at the same time.

Several embodiments of the invention have been described above with reference to the enclosed drawings. It will be realized that the different features may be combined in different manners than indicated and such other combinations are within the scope of the invention. The invention is only limited by the appended patent claims.

What is claimed is:

1. A method for producing a sterile medical solution comprising:

providing at least two components, a first component for said solution including bicarbonate ions and a second component for said component including glucose or calcium ions;

preheating said first component to a first temperature and said second component to a second temperature;

heat sterilizing said first and second components separately to a third and fourth temperatures respectively, said third and fourth temperatures comprising sterilizing temperatures for said first and second components;

maintaining said first and second components approximately at their respective third and fourth temperatures, so as to sterilize said first and second components;

cooling said first and second components; and delivering said first and second components to a mixing device.

2. The method of claim 1, wherein said heat sterilization step includes passing said first and second components separately through a heat sterilizing device.

3. The method of claim 1, wherein each of said at least two components is provided as a concentrate to be mixed with water before or after said passing step.

4. The method of claim 3, wherein said second component includes glucose at a pH of below at least 5.

5. The method of claim 4, wherein said second component includes glucose at a pH of below at least 4.

6. The method of claim 4, wherein said second component includes glucose at a pH of below at least 3.2.

7. The method of claim 1, further comprising:

providing said at least two components in concentrated form;

providing a flow of water; and introducing one of said at least two concentrated components into said flow of water prior to said heat sterilization step.

8. The method of claim 7, further comprising introducing a second of said at least two concentrated components into said flow of water prior to said heat sterilization step.

9. The method of claim 1, wherein one of said at least two components includes electrolytes selected from the group consisting of sodium chloride, calcium chloride, magnesium chloride, potassium chloride, sodium bicarbonate, sodium lactate and glucose.

10. An apparatus for producing a sterile medical solution comprising:
- at least two containers having at least a first component including bicarbonate ions and a second component including glucose or calcium ions;
- a first preheating device for heating said first component to a first temperature;
- a second preheating device for heating said second component to a second temperature;
- a heat sterilizing device for sterilizing said first and second components separately through said heat sterilizing device, where said heat sterilizing device heats and maintains said first and second components at a third and fourth temperature respectively, said third and fourth temperatures comprising sterilization temperatures for said first and second components;
- a cooling device for cooling said components; and
- a mixing device for receiving said components.

11. The apparatus of claim 10, wherein each component is provided as a concentrate to be mixed with substantially water before or after entering said heat sterilizing device.

12. The apparatus of claim 10, wherein one of said components includes glucose at a pH of below at least 5.

13. The apparatus of claim 12, wherein one of said components includes glucose at a pH of below at least 4.

14. The apparatus of claim 12, wherein one of said components includes glucose at a pH of below at least 3.2.

15. The apparatus of claim 10, further comprising:
- at least three components in concentrated form;
- a flow of water; and
- an introduction device for introducing at least one of said concentrated components into said flow of water.

16. The apparatus of claim 15, wherein a second concentrated component is provided to said flow of water prior to said heat sterilizer.

17. The apparatus of claim 10, wherein one of said first and second components includes electrolytes selected from the group consisting of sodium chloride, calcium chloride, magnesium chloride, potassium chloride, sodium bicarbonate, sodium lactate and glucose.

* * * * *